(12) United States Patent
Sato et al.

(10) Patent No.: US 9,060,981 B2
(45) Date of Patent: Jun. 23, 2015

(54) MARKER ASSOCIATED WITH NON-ALCOHOLIC STEATOHEPATITIS

(75) Inventors: Ayumi Sato, Shizuoka (JP); Tsuyoshi Harada, Tokyo (JP); Takashi Yano, Shizuoka (JP); Yoko Wakabayashi, Tokyo (JP)

(73) Assignee: MOCHIDA PHARMACEUTICAL CO., LTD., Tokyo (JP)

( * ) Notice: Subject to any disclaimer, the term of this patent is extended or adjusted under 35 U.S.C. 154(b) by 141 days.

(21) Appl. No.: 13/500,753

(22) PCT Filed: Oct. 15, 2010

(86) PCT No.: PCT/JP2010/068168
§ 371 (c)(1),
(2), (4) Date: May 8, 2012

(87) PCT Pub. No.: WO2011/046204
PCT Pub. Date: Apr. 21, 2011

(65) Prior Publication Data
US 2012/0231471 A1    Sep. 13, 2012

(30) Foreign Application Priority Data
Oct. 16, 2009 (JP) ................................ 2009-239570

(51) Int. Cl.
| | | |
|---|---|---|
| G01N 33/53 | (2006.01) | |
| A61K 31/202 | (2006.01) | |
| G01N 33/576 | (2006.01) | |
| G01N 33/68 | (2006.01) | |

(52) U.S. Cl.
CPC ............ *A61K 31/202* (2013.01); *G01N 33/576* (2013.01); *G01N 33/6893* (2013.01); *G01N 2800/044* (2013.01); *G01N 2800/52* (2013.01); *G01N 2800/56* (2013.01); *G01N 2800/60* (2013.01)

(58) Field of Classification Search
None
See application file for complete search history.

(56) References Cited

U.S. PATENT DOCUMENTS

| | | | |
|---|---|---|---|
| 5,019,508 | A | 5/1991 | Johnson et al. |
| 7,897,591 | B2 | 3/2011 | Puder et al. |
| 2007/0218519 | A1 | 9/2007 | Urdea et al. |
| 2009/0297546 | A1 | 12/2009 | Yamada et al. |

FOREIGN PATENT DOCUMENTS

| | | |
|---|---|---|
| EP | 1 582 873 A1 | 10/2005 |
| JP | 2000-102399 A | 4/2000 |
| JP | 2007-236253 A | 9/2007 |
| JP | 2007-315752 A | 12/2007 |
| JP | 2009-120607 A | 6/2009 |
| WO | WO 2007/016390 A1 | 2/2007 |
| WO | WO 2008/075788 A1 | 6/2008 |
| WO | WO 2009/028457 A1 | 3/2009 |

OTHER PUBLICATIONS

Haukeland et al., "Systemic inflammation in nonalcoholic fatty liver disease is characterized by elevated levels of CCL2", Journal of Hepatology, Jun. 2006, vol. 44, No. 6, pp. 1167-1174.
Horie at al., "Hepatocyte-specific pten deficiency results in steatohepatitis and hepatocellular carcinoma, and Insulin Hypersensitivity", Hepatology, Oct. 2004, No. 609, p. 428A.
International Search Report, PCT/JP2010/068168, Jan. 25, 2011.
Jin et al., "Telmisartan prevents hepatic fibrosis and enzyme-altered lesions in liver cirrhosis rat induced by a choline-deficient L-amino acid-defined diet", Biochemical and Biophysical Research Communications, Dec. 28, 2007, vol. 364, No. 4, pp. 801-807.
Kurita at al., "Olmesartan ameliorates a dietary rat model of nonalcoholic steatohepatitis through its pleiotropic effects", European Journal of Pharmacology, Jul. 7, 2008, vol. 588, Nos. 2-3, pp. 316-324.
Schmilovitz-Weiss et al., "Role of circulating soluble CD40 as an apoptotic marker in liver disease", Apoptosis, 2004, vol. 9, No. 2, pp. 205-210.
Tanaka et al., "Highly purified eicosapentaenoic acid treatment improves nonalcoholic steatohepatitis", Journal of Clinical Gastroenterology, Apr. 2008, vol. 42, No. 4, pp. 413-418.
The Japan Society of Hepatology ed., "NASH•NAFLD no Shinryo Gaido (Guidelines for Diagnosis and Treatment of NASH and NAFLD)", Bunkodo Co., Ltd., Aug. 22, 2006, and its partial translation.
English translation of International Preliminary Report on Patentabity and Written Opinion issued May 24, 2012, in PCT International Application No. PCT/JP2010/068168.
Chatzigeorgiou et al., "Plasma and urine soluble CD40 (sCD40) in children and adolescents with type1 diabetes mellitus (T1DM). A possible pathway to diabetic angiopathy," FEBS Journal (2008), vol. 275 (Suppl. 1), PP7A-14, p. 303 (abstract).
Database Biosis [Online] Bioscience Information Service. Philadelphia, PA, US (Nov. 2008): Cayon et al.; "Gene expression in obese patients with non-alcoholic steatohepatitis," XP002700444, Database Accession No. PREV200800490452 "abstract".
Database Biosis [Online] Biosoiences Information Services, Philadelphia, PA, US (Apr. 2006); Gurhan et al., "The Effects of Atorvastatin on Hematological and Inflammatory Parameters," XP002700442, Database Accession No. PREV200900258247 "abstract".
Estep et al., "Expression of Cytokine Signaling Genes in Morbidly Obese Patients with Non-Alcoholic Steatohepatitis and Hepatic Fibrosis," Obes. Surg. (2009), vol. 18, pp. 617-624.

(Continued)

*Primary Examiner* — Michael Pak
(74) *Attorney, Agent, or Firm* — Birch, Stewart, Kolasch & Birch, LLP

(57) ABSTRACT

Disclosed is a novel NASH marker for use in a method for detecting NASH or evaluating the severity of NASH, which utilizes at least one factor selected from the group consisting of an IL-1 receptor antagonist, sCD40, HMGB1, sPLA2 group IIA and an sPLA2 activity as the marker. Also disclosed is a method for detecting NASH or evaluating the severity of NASH in a subject, which utilizes the marker.

3 Claims, 3 Drawing Sheets

(56) References Cited

OTHER PUBLICATIONS

Extended European Search Report issued Jul. 23, 2015, in European Patent Application No. 10823472.5.

Forst et al., "Improved plaque stability and reduced inflammation during pioglitazone treatment in type 2 diabetic patients with CHD," Diabetes (Jun. 2007), vol. 56, Suppl. 1, 647-P, p. A172.

Forst et al., "Pleiotrophic and anti-inflammatory effects of pioglitazone precede the metabolic activity in type 2 diabetic patients with coronary artery disease," Atherosclerosis (2008), vol. 197, pp. 311-317.

Mason et al., "Effect of Enhanced Glycemic Control with Saxagliptin on Endothelial Nitric Oxide Release and CD40 Levels in Obese Rats," J. Artheroscler. Thromb. (2011), vol. 18, pp. 774-783.

Varo et al., "Elevated Plasma Levels of the Atherogenic Mediator Soluble CD40 Ligand in Diabetic Patients," Circulation (2003), vol. 107, pp. 2664-2669.

Yoneda et al., "Plasma Pentraxin3 is a Novel Marker for Nonalcoholic Steatohepatitis (NASH)," BMC Gastroenterology (2008), vol. 8, p. 53.

Carpentier et al., "n-3 Fatty acids and the metabolic syndrome," Am. J. Clin. Nutr. (2006), vol. 83 (suppl), pp. 1499S-1504S.

Communication Pursuant to Article 94(3) EPC issued May 16, 2014, in European Patent Application No. 10823472.5.

Kudo et al., "Lipopolysaccharide triggered TNF-$\alpha$-induced hepatocyte apoptosis in a murine non-alcoholic steatohepatitis model," Journal of Hepatology (2009), vol. 51, pp. 168-175.

Valva et al., "Apoptosis markers in liver biopsy of nonalcoholic steatohepatitis in pediatric patients," Human Pathology (2008), vol. 39, pp. 1816-1822.

Notification of Reasons for Refusal issued Nov. 4, 2014, in Japanese Patent Application No. 2011-536192, with English translation.

MARKER ASSOCIATED WITH NON-ALCOHOLIC STEATOHEPATITIS

TECHNICAL FIELD

This invention relates to a method for detecting fatty liver disease, and in particular, non-alcoholic fatty liver disease or non-alcoholic steatohepatitis; a method for detecting such disease by using a marker which is an index for seriousness; and a method for evaluating seriousness of or therapeutic effects on such disease. This invention also relates to a method for treating the non-alcoholic steatohepatitis including use of such marker for the evaluation, and a kit for conducting the evaluation using such marker.

BACKGROUND ART

A disease group including liver disorders from simple fatty liver to steatohepatitis, fibrosis, and liver cirrhosis occurring at those without drinking history excluding viral liver diseases, autoimmune liver diseases, and metabolic liver diseases such as hemochromatosis and Wilson's disease is generally defined as non-alcoholic fatty liver disease (hereinafter abbreviated as NAFLD). NAFLD is further divided by liver biopsy (pathological finding) into simple fatty liver which is generally conceived to have a favorable prognosis and non-alcoholic steatohepatitis (hereinafter abbreviated as NASH) with unfavorable prognosis, and the NASH is considered to be the serious type of the NAFLD. The pathologies of the inflammation, fat accumulation, fibrosis or liver cirrhosis, and liver cancer determined to be NASH by the liver biopsy are the same as those caused by other causes, and many hepatitis cases which have been denied for the alcoholic liver disorder, viral hepatitis, and drug-induced liver injury are estimated to be the pathological conditions of the NASH. In the U.S., 20% of the population is estimated to suffer from the NAFLD, and 3% is estimated to suffer from the NASH. These are also diseases frequently encountered in Japanese general practice. Frequency of the NAFLD in medical examination is 8%, and the frequency of NASH is estimated to be at least 0.5 to 1% in the adult. In Japan, obese adults with BMI of 25 or more include 13 million men and 10 million women, and presence of 5 to million NAFLD patients and about 300 to 500 thousand NASH patients is estimated from these figures. Furthermore, in the case of the NAFLD, frequency of dyslipidemia complication is about 50%, frequency of hypertension complication is about 30%, frequency of hyperglycemia complication is about 30%, and frequency of metabolic syndrome complication is about 40% based on the diagnostic criteria of the metabolic syndrome, and from now on, increase in the number of NASH cases and expansion of the disease to younger people are estimated to take place with the increase of the lifestyle disease. In some patients, the liver disorder proceeds via the hepatitis to the liver cirrhosis or liver cancer by the activation of hepatic stellate cells, and this is clinically problematic. At present, histological diagnosis by liver biopsy is conceived to be necessary for definitive diagnosis of the NASH, and the histological diagnosis by the liver biopsy is also conceived to be necessary for the diagnosis of the healing of the disease. Liver biopsy is associated with the problem of heavy physical burden for both patients and medical professionals, and there is a strong demand for the establishment of a characteristic blood marker which is useful for the diagnosis and evaluation of the pathological conditions of the NAFLD and the NASH which can be used instead of the liver biopsy requiring the invasion. In addition, there is no established therapeutic method at present for the NASH while various treatments are attempted for improving the pathological conditions of the NASH and their effectiveness is reported (see Non-Patent Literature 1).

Examples of the blood test index which has been used for detecting the NASH include aspartate aminotransferase (hereinafter also referred to as AST), alanine aminotransferase (hereinafter also referred to as ALT), AST/ALT ratio, serum ferritin, serum thioredoxin, HOMA-IR, platelet count, TNFα, adiponectin, leptin, high sensitivity CRP, hyaluronic acid, type IV collagen 7S, procollagen III polypeptide, and CK18 fragment.

Also reported is increase of TNFα and CCL2/MCP-1 in the NASH patients compared to the patients of simple fatty acid (see Non-Patent Literature 2).

It has also been reported that when telmisartan (see Non-Patent Literature 3) or olmesartan (see Non-Patent Literature 4) was administered to a NASH model animal, fibrosis of the liver was suppressed, and this also led decrease in the expression of TIMP1 and TIMP2 mRNAs in the liver tissue (see Non-Patent Literature 3) or the expression of alpha 1[I] procollagen gene in the liver (see Non-Patent Literature 4).

In the gene analysis of liver cell in the liver cell-specific Pten knockout mouse which is a model animal for steatohepatitis and canceration of the liver, induction of adipsin, adiponectin, and the like was also reported (see Non-Patent Literature 5).

Also proposed is administration of a matrix metalloprotease (MMP) inhibitor to the NASH and the NAFLD (see Patent Literature 1).

Tanaka et al. examines amelioration of NASH by 12 month administration of high purity ethyl icosapentate (hereinafter also referred to as EPA-E). This study shows the results of liver biopsy after the EPA-E administration period, enzymatic observation using AST and ALT, and evaluation by inflammatory cytokines such as TNFα, sTNF-R1, and sTNF-R2 and oxidation stress markers such as thioredoxin (see Non-Patent Literature 6).

CITATION LIST

Patent Literature

Patent Literature 1: WO 2007/016390

Non-Patent Literature

Non-Patent Literature 1: The Japan Society of Hepatology ed., "NASH•NAFLD no Shinryo Gaido (Guidelines for Diagnosis and Treatment of NASH and NAFLD)," BUNKODO CO., LTD., Aug. 22, 2006.
Non-Patent Literature 2: J. Hepatol. 2006 June; 44 (6): 1167-1174.
Non-Patent Literature 3: Biochem Biophys Res Commun. 2007 Dec. 28; 364 (4): 801-807.
Non-Patent Literature 4: Eur J. Pharmacol. 2008 Jul. 7; 588 (2-3): 316-324.
Non-Patent Literature 5: Hepatology October 2004 428A 609.
Non-Patent Literature 6: Journal of Clinical Gastroenterology, 2008, Vol. 42, No. 4, 413-418.

SUMMARY OF INVENTION

Technical Problems

An object of the present invention is to provide a marker which is useful for detecting NASH or evaluating seriousness of the NASH. Another object of the present invention is to provide a marker which is useful for evaluating therapeutic effects of the pharmaceutical composition containing a NASH therapeutic agent, and in particular, EPA-E as its effective component. A further object of the present invention is to provide a method for detecting NASH, a method for evaluating seriousness of the NASH, and a method for evaluating therapeutic effects on the NASH using the marker. A still further object of the present invention is to provide a method for treating the subject who has been detected or evaluated for the NASH using the marker of the present invention. A still further object of the present invention is to provide an assay kit inducing a marker which is useful for detecting NASH or evaluating seriousness of the NASH.

Solution to Problems

In order to obviate the problems as described above, the inventors of the present invention conducted an intensive study, and found that amount or activity of particular biological factors is different in healthy subjects and the NASH patients. While these factors can each be measured in terms of the amount or the activity of the protein by a method known in the art, their use as a NASH marker has never been reported. The amount and the activity of such factors in the NASH patients have been confirmed to be relevant with the AST value which is a known index for hepatic dysfunction, and accordingly, it has been found that these factors can serve as new markers useful for detecting the NASH and evaluating the seriousness of and therapeutic effects on the NASH. The present invention has been achieved on the basis of such finding.

The present invention also provides second factors as a marker. The second factors are selected as a factor indicating the NASH and NAFLD-suppressing effects of EPA-E by the gene analysis in mouse which is described in the section of Examples. The second factors are factors whose expression alters in the liver of mice which develop serious fatty liver after being fed with a high fat, high sugar diet, and these factors are also those selected from group of genes whose expression was suppressed by the EPA-E administration. The second factor group includes factors which have been conceived as a NASH marker, and the second factor group is expected to be useful as a NASH marker. The second factor group may be used in addition to the factors of the NASH marker as described above. More specifically, the second factors should be useful as a marker allowing evaluation of the NASH therapeutic effects of a member of the group consisting of icosapentaenoic acid and its pharmaceutically acceptable salts and esters (hereinafter also generally referred to as EPAs) in view of the confirmation of the relevance between the second factors and the therapeutic effects of EPA-E.

Accordingly, the present invention provides a method for detecting the NASH and a method for evaluating seriousness of and therapeutic effects on the NASH by using the marker of the present invention. The present invention also provides a therapeutic method including administration of a NASH therapeutic agent to the subject who has been detected or evaluated for the NASH by using the marker of the present invention or a method for treating NASH involving the evaluation of the NASH therapeutic effects using the marker of the present invention as a new therapeutic method. The therapeutic agent used for the NASH in the present invention is preferably a member selected from EPAs. More specifically, the second factors may be used as an index for selecting subjects who are suitable for the therapy using EPAs from NASH and/or NAFLD subjects, or as an index which individual subject can use in selecting the therapy using EPAs from various therapies of the NASH in view of the confirmation of the relevance between the second factors and the effects of EPA-E.

Next, exemplary embodiments of the present invention as described above are described.

(1) A method for detecting NASH or evaluating seriousness of NASH using at least one factor selected from the group consisting of IL-1 receptor antagonist, sCD40, HMGB1, sPLA2 group IIA, and sPLA2 activity as a marker.

The IL-1 receptor antagonist, sCD40, HMGB1, or sPLA2 group IIA is preferably in the form of an antigen. The method of (1) is preferably a method for detecting the NASH.

(2) A method according to the above (1) comprising the step of measuring the factor of the above (1) in a biological specimen from a subject.

(3) A method according to the above (1) or (2) comprising the steps of
 A) measuring amount and/or activity level of the factor in the biological specimen from the subject, and
 B) comparing the value measured in the step A) with a cut off value.

(4) A method according to the above (3) which is a method for detecting presence of the NASH wherein the subject is determined positive for the NASH when the result of the comparison of the value measured for the subject with the cut off value is positive in the B).

(5) A method for detecting NASH or evaluating seriousness of the NASH comprising the step of measuring at least one member selected from the second factor group consisting of IL-2, apolipoprotein A-IV, apolipoprotein C-II, CCL2, thrombospondin 1, trehalase, MMP12, MMP13, TIMP1, complement factor D, lipoprotein lipase, alpha chain of IL-3 receptor, locus D of lymphocyte antigen 6 complex, COL1a1, member 19 of TNFR superfamily (TAJ), TNFAIP6, VLDLR, members 1, 2, 3, and 12 of EarA family, INSL5, TGF β2, HAMP, lipase H, and CYP7B1 in the biological specimen from the subject as a marker.

The factor is preferably in the form of an antigen.

(6) A method according to any one of the above (1) to (4) wherein at least one member selected from the second factor group of the above (5) in the biological specimen from the subject is used as another marker.

(7) A method according to the above (5) or (6) wherein the second factor group consists of IL-2, apolipoprotein A-IV, apolipoprotein C-II, CCL2, thrombospondin 1, MMP12, MMP13, trehalase, TIMP1, complement factor D, lipoprotein lipase, HAMP, and lipase H.

(8) A method for evaluating therapeutic effects for NASH comprising the steps of conducting measurement of at least one factor selected from the group consisting of IL-1 receptor antagonist, sCD40, HMGB1, sPLA2 group IIA, sPLA2 activity, and the second factor group in a biological specimen from a subject as a marker at least twice at a certain interval, and comparing the measured values to thereby evaluate the therapeutic effect.

(9) A method for evaluating therapeutic effects for NASH comprising the steps of
 A) measuring at least one factor selected from the group consisting of IL-1 receptor antagonist, sCD40, HMGB1, sPLA2 group IIA, sPLA2 activity, and the second factor group in a biological specimen from a subject as a marker,
 B) treating the non-alcoholic steatohepatitis, C) measuring the factor which is the same as the one used in A) in the biological specimen from the subject at a certain interval from the measurement of the A), and D) comparing the values obtained in the A) and C).

(10) A method according to (8) or (9) for evaluating therapeutic effects of a NASH therapeutic agent, further comprising the step of administering the NASH therapeutic agent for treating the NASH.

(11) A method according to (10) wherein the NASH therapeutic agent is a pharmaceutical composition containing at least one member selected from the EPAs as its effective component, and at least one member selected from the second factor group is used for the marker.

(12) A method for treating NASH comprising the steps of
1) conducting detection or evaluation of the seriousness of the NASH of a subject by any one of the methods (1) to (7), and
2) conducting the NASH treatment of the subject whose NASH has been detected or evaluated in 1).

(13) A therapeutic method according to (12) further comprising the step of
3) conducting the method for evaluating therapeutic effects for NASH of the above (8) or (9).

(14) A therapeutic method according to (13) further comprising the step of
4) determining the therapeutic method of the subject based on the evaluation of the therapeutic effect.

(15) A therapeutic method according to any one of (12) to (14) wherein the NASH treatment is administration of a pharmaceutical composition containing at least one member selected from EPAs.

(16) A therapeutic method according to (15) wherein the method for evaluating therapeutic effects for NASH is conducted by using at least one member selected from at least the second factor group for the marker.

(17) A method for treating non-alcoholic steatohepatitis comprising the step of administering an effective amount of NASH therapeutic agent to a subject whose non-alcoholic steatohepatitis has been indicated by at least one factor selected from the group consisting of IL-1 receptor antagonist, sCD40, HMGB1, sPLA2 group IIA, and sPLA2 activity in a biological specimen from the subject.

(18) A method according to (17) wherein the NASH therapeutic agent is a pharmaceutical composition containing at least one member selected from EPAs as its effective component.

(19) A method according to (1) to (18) wherein at least one member selected from the group consisting of additional test indexes is used for the detection or the evaluation.

(20) A method for selecting NASH treatment using EPAs by using at least one factor selected from the group consisting of IL-1 receptor antagonist, sCD40, HMGB1, sPLA2 group IIA, sPLA2 activity, and the second factor group in the biological specimen from the subject for the marker.

(21) A method for treating NASH comprising the step of administering a pharmaceutical composition containing at least one member selected from EPAs as its effective component to the subject who has been selected to be suitable for the NASH treatment with EPAs by (20).

(22) A method for selecting a subject who is suitable for NASH treatment with EPAs from NASH and/or NAFLD subjects by using at least one factor selected from the group consisting of IL-1 receptor antagonist, sCD40, HMGB1, sPLA2 group IIA, sPLA2 activity, and the second factor group in the biological specimen from the subject for the marker.

(23) A method for treating NASH comprising the step of administering a pharmaceutical composition containing at least one member selected from EPAs as its effective component to the subject who has been selected to be suitable for the NASH treatment with EPAs by (22).

(24) An assay kit for detecting NASH or evaluating seriousness of or therapeutic effects on NASH comprising an antibody or a fragment thereof against at least one member selected from the group consisting of IL-1 receptor antagonist, sCD40, HMGB1, sPLA2 group IIA, IL-2, apolipoprotein A-IV, apolipoprotein C-II, CCL2, thrombospondin 1, trehalase, MMP12, MMP13, TIMP1, complement factor D, lipoprotein lipase, alpha chain of IL-3 receptor, locus D of lymphocyte antigen 6 complex, COL1a1, member 19 of TNFR superfamily (TAJ), TNFAIP6, VLDLR, members 1, 2, 3, and 12 of EarA family, INSL5, TGF β2, HAMP, lipase H, and CYP7B1 and/or a substrate for measuring sPLA2 activity.

(25) A marker for detecting NASH or evaluating seriousness of NASH wherein the marker comprises at least one factor selected from the group consisting of IL-1 receptor antagonist, sCD40, HMGB1, sPLA2 group IIA and sPLA2 activity.

(26) A marker for detecting NASH or evaluating seriousness of the NASH comprising at least one member selected from the second factor group consisting of IL-2, apolipoprotein A-IV, apolipoprotein C-II, CCL2, thrombospondin 1, trehalase, MMP12, MMP13, TIMP1, complement factor D, lipoprotein lipase, alpha chain of IL-3 receptor, locus D of lymphocyte antigen 6 complex, COL1a1, member 19 of TNFR superfamily (TAJ), TNFAIP6, VLDLR, members 1, 2, 3, and 12 of EarA family, INSL5, TGF β2, HAMP, lipase H, and CYP7B1.

(27) At least one factor for use as a marker for detecting NASH or evaluating seriousness of the NASH, the factor being selected from the group consisting of IL-1 receptor antagonist, sCD40, HMGB1, sPLA2 group IIA, and sPLA2 activity.

(28) At least one substance for use as a marker for detecting NASH or evaluating seriousness of the NASH, the substance being selected from the second factor group consisting of IL-2, apolipoprotein A-IV, apolipoprotein C-II, CCL2, thrombospondin 1, trehalase, MMP12, MMP13, TIMP1, complement factor D, lipoprotein lipase, alpha chain of IL-3 receptor, locus D of lymphocyte antigen 6 complex, COL1a1, member 19 of TNFR superfamily (TAJ), TNFAIP6, VLDLR, members 1, 2, 3, and 12 of EarA family, INSL5, TGF β2, HAMP, lipase H, and CYP7B1.

Advantageous Effects of Invention

The present invention provides an index useful for the detection or diagnosis of the NASH as well as evaluation of the seriousness of or therapeutic effects on the NASH, and as a consequence, convenient detection of the NASH candidate subjects as well as evaluation of the seriousness of and therapeutic effects on the NASH and NAFLD have been enabled.

More specifically, convenient evaluation of the therapeutic effects has been enabled in the treatment of the NASH with EPAs, and this has eliminated the need for biopsy, and hence, reduced burden of the patients as well as medical professionals.

DESCRIPTION OF EMBODIMENTS

Figure 1:
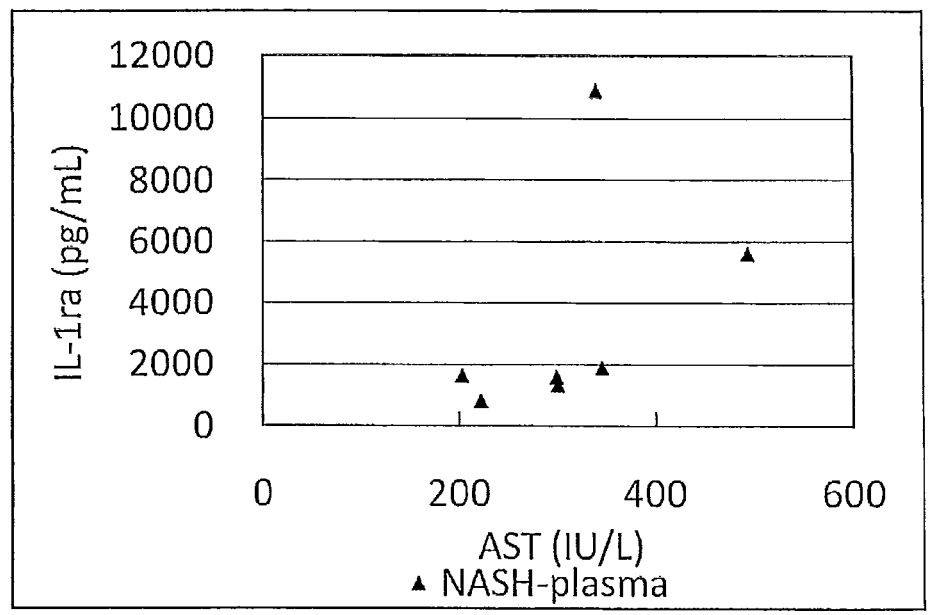
FIG. 1 is a graph showing IL-1ra value in plasma in relation to plasma AST value of the NASH patients.

Next, the present invention is described in further detail.

1. Marker

The marker according to the present invention may be any of gene, protein, or activity as long as it is measurable as a factor in a biological specimen. The marker is preferably a factor which can be conveniently measured in blood, and more preferably a protein, and still more preferably, an antigen which can be measured by using an antibody.

<First Factor Group>

The present invention provides IL-1 receptor antagonist, sCD40, HMGB1, sPLA2 group IIA, and sPLA2 activity as a NASH marker, and for the convenience of the explanation, at least one factor selected from this factor group is occasionally referred to as a first factor or a first marker. The first factor is a factor which can be detected with a known assay kit by using a biological specimen as the analyte. The NASH marker may be detected as a biologically active protein, and preferably, as an antigen. Use of such factor as a NASH marker has never been reported, and these markers are novel markers for diagnosis or detection of the NASH or evaluation of seriousness of or therapeutic effects on the NASH. The present invention is hereinafter described in detail, and in the present specification, the diagnosis, detection, or the evaluation of the seriousness or therapeutic effects may be simply referred to as the evaluation.

IL-1 Receptor Antagonist (IL-1ra): an Interleukin-1 Receptor Antagonist

IL-1 is a typical inflammatory cytokine as in the case of TNFα. IL-1ra is an endogenous anti-inflammatory cytokine, and inhibits agonist activity of IL-1 by competing with the IL-1.

It has been reported that an IL-1ra knockout mouse exhibits excessive IL-1 signal transduction, and such mouse administered with the arteriosclerosis diet exhibits NASH-like liver histological image and hypercholesteteremia (Nihon Rinsho Vol. 64 No. 6 (2006-6) pages 1063-1070). From this report, it would be estimated that IL-1ra in the NASH patient body is at a reduced level.

In the present invention, the inventors compared concentration of the IL-1ra in plasma between the NASH patients and the healthy subjects. Contrary to the estimation, the plasma IL-1ra concentration in the NASH patients was significantly higher than the plasma IL-1ra concentration the healthy subjects. Accordingly, usefulness of the IL-1ra for a NASH marker in the present invention was demonstrated.

Soluble CD40 (sCD40)

CD40 is a 50 kDa membrane-bound glycoprotein of TNF receptor superfamily. CD40 is expressed in various cells, and it plays an important role in controlling various immunoreactions and apoptosis.

It has been reported that average sCD40 level in serum of subjects suffering from a liver disease is 112.9, which is higher than the 24.2 in the healthy subjects. The liver diseases in this report included viral hepatitis (59 cases), cholestatic hepatitis (20 cases), AIH (autoimmune hepatitis) (7 cases), alcoholic hepatitis (7 cases), idiopathic liver disease (7 cases), fulminant hepatitis (4 cases), hepatocellular carcinoma (7 cases), sarcoidosis (2 cases), and Wilson's disease (1 case). When the sCD40 concentration was compared among the diseases, the sCD40 concentration in the alcoholic liver disease whose pathology is accepted to be close to the NASH was 12.6, and this value was lower than that of the healthy subjects (Apoptosis 2004; 9: 205-210). From this report, sCD40 level of the NASH patient was expected to be equal to or lower than the healthy subjects.

There has also been reported that the cell death after 24 hour exposure of FaO cell (liver cancer cell) to lipid emulsion was necrosis, and not apoptosis (Nutrition 25 (2009) 200-208).

In the present invention, we compared the sCD40 concentration in plasma between the NASH patients and the healthy subjects, and contrary to the expectation, the plasma sCD40 concentration in the NASH patients was significantly higher than that of the healthy subjects. Usefulness of the sCD40 for the NASH marker was thereby indicated.

HMGB1 (High Mobility Group Box 1)

HMGB1 is a protein having a molecular weight of 30 kDa, which is expressed in various cells. HMGB1 has the action of binding and stabilizing the DNA and action as a cytokine, and HMGB1 is also called a cell necrosis marker.

Evaluation of HMGB1 using an in vitro fatty liver model prepared by exposing FaO cell (liver cancer cell) to a lipid emulsion for a certain period has been reported.

Exposure of the FaO cell (liver cancer cell) to the lipid emulsion for 6 hours resulted in marked increase of ROS production in the cell. HMGB1 was used as a marker for necrotic cell death, and when the FaO cell was exposed to the lipid emulsion for 24 hours, decrease in the HMGB1 was observed. Caspase 3 activity was used as a marker for apoptotic cell death, and 24 hour exposure did not result in the change of the caspase 3 activity. Accordingly, the liver cell death was concluded to be necrosis (Nutrition 25 (2009) 200-208).

In the present invention, we measured plasma HMGB1 concentration in both NASH patients and healthy subjects, and significant increase of the HMGB1 concentration was found in the NASH patient plasma. The present invention has for the first time revealed that plasma HMGB1 of the subject can be used as a NASH marker.

sPLA2 (Secretory Phospholipase A2) Group IIA: Type 2A, Type IIA

Phopholipases A2 (PLA2s) are enzymes constituting a superfamily, each of which hydrolyzes ester bond at position 2 of a phosphoglyceride to release a free fatty acid and a lysophospholipid. sPLA2 is a secretory enzyme, and classified into subtypes such as Group IA, IB, IIA, IIB, IIC-III, V, VII, IX, and the like depending on the molecular weight and $Ca^{2+}$ dependency. Presence of sPLA2 group IIA has been confirmed in human synovia and platelet, and involvement in inflammation has been indicated (Dennis E. A. et al., Trends Biochem. Sci. 22, 1-2 (1997)).

Relevance of the sPLA2 group IIA with hyperchlosterolemia transgenic mouse expressing human sPLA2 group II gene has been reported. When human sPLA2 group II transgenic mice and non-transgenic mice (n=10) were fed with 1% cholesterol-rich diet for 13 weeks, plasma cholesterol level of the sPLA2 group II transgenic mice decreased compared to the non-transgenic control, and in the liver tissue, concentration of free cholesterol and esterified cholesterol increased with no change in the triglyceride concentration. Based on these results, authors of this literature discuss that "it has been indicated that excessive expression of the sPLA2 group IIA increases transportation of cholesterol to the liver. This mechanism may contribute for the progress of hypercholesterolemia in the patients suffering from inflammatory disease", indicating the relevance of the sPLA2 group IIA with the hyperchlosterolemia (Inflammation Vol. 28 No. 2 (2004)).

However, relevance of the sPLA2 group IIA with the NASH has never been known, and dynamism of the concentration of sPLA2 group IIA in the plasma of human NASH patient has never been estimated.

In the present invention, we measured concentration of sPLA2 group IIA in the plasma from NASH patients and healthy subjects, and found that concentration of sPLA2 group IIA in the NASH patient plasma exhibits significant increase compared to the healthy subjects. The present invention has for the first time revealed that sPLA2 group IIA in the plasma of a subject can be used as a NASH marker.

sPLA2 Activity

As described above, several subtypes are present in the secretory phospholipases A2 (sPLA2s), and we measured activity of the entire sPLA2 in plasma.

Expression of the sPLA2 increases in atheromatous plaque, and reportedly, sPLA2 promotes production of inflammatory lipid such as lysophospholipid by the hydrolysis of LDL, and accordingly, sPLA2 is indicated to be relevant with atherosclerosis, inflammation, and the like (Oestvang J et al., Biochim Biophys Acta. 2006 November; 1761 (11): 1309-16).

In addition, the literature as mentioned above (Inflammation, Vol. 28, No. 2 (2004)) discloses that sPLA2 activity in plasma increased in the transgenic mouse exhibiting high expression of the sPLA2 group II.

There is so far no report that studied the relevance of the sPLA2 activity with the NASH. However, if estimation is made from what have been reported on the sPLA2 activity, increase of sPLA2 activity would be estimated in view of the increase of inflammatory indexes such as TNFα in the NASH patient.

In the present invention, the sPLA2 activity in plasma was compared between the NASH patients and the healthy subjects, and contrary to the expectation, the sPLA2 activity in the plasma from the NASH patients was significantly lower than that of the healthy subjects.

The present invention has for the first time revealed that sPLA2 activity can be used as a NASH marker.

<Second Factor Group>

The markers of the second factor group of the present invention are group of factors selected by the following procedure.

(1) Serious fatty liver was induced when mice were fed with high fat, high sugar diet+5% ethyl palmitate for 20 weeks (HF-HS group) while fatty liver was not induced when the mice were fed with high fat, high sugar diet+5% EPA-E in similar manner (EPA group).

(2) Next, expression of genes in the liver was compared in 3 groups, namely, the control group fed with normal diet, the HF-HS group, and the EPA group. The genes exhibiting different expression both between the control group and the HF-HS group, and between the HF-HS group and the EPA group were selected.

(3) In addition, the factors whose corresponding proteins may be secreted in the blood and which may be relevant with the NASH were selected from these genes.

The following two groups (A) and (B) are selected based on the comparison of genes between the groups in the above (2) as will be described in detail in Example 2.

(A) HF-HS group/control group ≥2 and EPA group/HF-HS group ≤0.5.

(B) HF-HS group/control group ≤0.5 and EPA group/HF-HS group ≥2.

In the above (3), relevance with the NASH may be any of relevance with lipid metabolism, relevance with inflammation, and increase in the expression in the liver of SREBP transgenic mouse.

Group (A) are markers which had been extracted based on the genes exhibiting increased expression in the liver of the mice with the fatty liver, but whose expression is suppressed by the EPA-E administration, and therefore, content in the biological specimen, and preferably, content in plasma increases in the case of NAFLD while the content decreases by the therapy administering the EPAs.

Group (B) are markers which had been extracted based on the genes exhibiting reduced expression in the liver of the mice with the fatty liver, but whose expression increases by the EPA-E administration, and therefore, content in the biological specimen, and preferably, content in plasma decreases in the case of NAFLD while the content increases by the therapy administering the EPAs.

These are factors whose expression changes in the development of the previous stage of the NASH, namely, at the stage of fatty liver (NAFLD), and therefore, these factors are useful in the detection, diagnosis, and evaluation of the seriousness of the NASH.

In the present invention, the term "NAFLD" is used to designate the non-alcoholic fatty liver diseases including the NASH. However, the term "NAFLD" can be also used to particularly designate the pathological conditions exhibiting the fatty liver as a previous stage of the NASH before reaching the stage of NASH.

These factors are also factors whose expression in the model mice changed with the suppression of the fatty liver by the EPA-E administration. Therefore, these factors are also useful as an index for evaluating the therapeutic effects of the administration of EPAs on the NASH. These factors can also be used as an index for selecting subjects who are suitable for the therapy involving administration of the EPAs from the NASH and/or NAFLD subjects, or an index for selecting subjects who should be administered with the EPAs, or at the level of the individual subject, as an index for selecting the therapy of administering the EPAs from various therapeutic methods of the NASH.

The factors selected as group (A) include IL-2, apolipoprotein A-IV, apolipoprotein C-II, CCL2, thrombospondin 1, trehalase, MMP12, MMP13, TIMP1, complement factor D, lipoprotein lipase, alpha chain of IL-3 receptor, locus D of lymphocyte antigen 6 complex, COL1a1, member 19 of TNFR superfamily (TAJ), TNFAIP6, VLDLR, and members 1, 2, 3, and 12 of EarA family.

The factors selected as group (B) include INSL5, TGF β2, HAMP, lipase H, and CYP7B1.

These factors are as described below.

IL-2: Interleukin 2

IL-2 is a cytokine involved in cellular immunity.

IL-2 has activities such as T cell proliferation and activation, B cell proliferation and antibody production-increasing ability, activation of monocyte and macrophage, proliferation and activation of natural killer cell (NK cell), induction of lymphokine-activated killer cell (LAK cell).

IL-2 is also conceived to be necessary for the maintenance of regulatory T cell (Treg).

Increase in the blood IL-2 level has been reported in the rat having fatty liver induced by feeding high fructose diet for 10 days (Clin Biochem. 2005 June; 38(6): 540-7).

Apolipoprotein A-IV

Apolipoprotein A-IV is a factor constituting chylomicron and high density lipoprotein. In type I diabetes model mice induced by streptozotocin and type II diabetes model ob/ob mice, increase in the level of mRNA of apolipoprotein A-IV in the liver and the level of serum protein compared to the control has been reported (J Lipid Res. 2006 November; 47(11): 2503-14).

Apolipoprotein C-II

Apolipoprotein C-II is an apoprotein which is critical in the expression of lipoprotein lipase which is an enzyme which hydrolyzes triglyceride in chylomicron and VLDL.

Increase of apolipoprotein C-II is recognized in types IIb, III, IV, and V hyperlipidemia (Nippon Rinsho Vol. 62, Suppl. 12 2004).

CCL2: Chemokine (C-C Motif) Ligand 2

CCL2 is a cytokine gene which is relevant with immune regulation and inflammation.

When CRP, TNFα, IL-6, CCL2/MCP-1, CCL19, CCL21, and the like in the serum sample of 22 cases of simple fatty liver and 25 cases of NASH were measured to clarify the role of systemic inflammation in NAFLD, increase in the IL-6, CCL2/MCP-1, and CCL19 compared to the healthy subjects was recognized in NAFLD patients. In NASH patients, increase in the TNFα and CCL2/MCP-1 compared to the patients of simple fatty liver is reported (Haukeland et al. J Hepatol. 2006 June; 44(6): 1167-1174).

Thrombospondin 1: TSP1

The protein coded by this gene is an adherence glycoprotein which mediates interactions between cells or between the cell and the matrix, and TSP1 is known to function in the course of platelet aggregation, angiogenesis, tumorigenesis, and the like.

When subcutaneous fat from 86 cases of non-diabetes subjects and visceral fat and subcutaneous fat from 14 cases of patients who have experienced surgery and 38 cases of subjects with abnormal glucose tolerance who have been administered with metformin or pioglitazone for 10 weeks were measured for TSP mRNA, and TSP1 mRNA was relevant with obesity (BMI), inflammation of adipocytes, and insulin resistance (Varma et al. Diabetes. 2008 February; 57(2): 432-9, Epub 2007, Dec. 5).

No case of blood thrombospondin 1 in NASH and NAFLD patients has been reported. In the present invention, however, increase in plasma from NAFLD patients of thrombospondin 1 (protein) was confirmed, and thrombospondin 1 was indicated to be a marker which can be assayed in blood.

IL-3 Receptor (Interleukin-3 Receptor), Alpha Chain

IL-3 receptor is a receptor having high affinity for IL-3, which is found in hematopoietic progenitor cell, bone marrow progenitor cell, and eosinophil, basophil.

IL-3 receptor is formed from a dimer comprising IL-3 receptor alpha subunit and beta subunit which is common between cytokine receptors.

Lymphocyte Antigen 6 Comlex, Locus D

Locus D of lymphocyte antigen 6 comlex is known to be expressed in keratinocyte.

MMP12 and MMP13: Atrix Metallopeptidase 12 and Atrix Metallopeptidase 13

MMP is an enzyme which decomposes extracelluar matrix. MMP12 which is mainly secreted from macrophage is believed to be relevant with various inflammatory diseases while MMP13 is involved in the decomposition of extracelluar matrix of skeletal tissues. Use of a matrix metalloproteinase inhibitor for NASH and NAFLD has been proposed (see Patent Literature 1).

Trehalase (Brush-Border Membrane Glycoprotein)

This gene codes for trehalase which hydrolyzes trehalose (a disaccharide).

Trehalase is an enzyme which hydrolyzes trehalose (a disaccharide) to produce glucose. Trehalase is widely found in nature, and trehalase is found not only in human plasma but also in various human tissues. Synthesis and decomposition of the trehalose (a substrate) is believed be relevant with carbohydrate transport mechanism.

TIMP1: Tissue Inhibitor of Metalloproteinase 1

Liver fibrosis was reported in NASH model rats induced by 8 weeks of choline-deficient, L-amino acid-deficient (CDAA) diet. However, after administering telmisartan (an angiotensin II type 1 receptor antagonist) for 10 weeks, expression of the mRNA of TIMP1 and TIMP 2 decreased indicating suppression of the liver fibrosis (Biochem Biophys Res Commun. 2007 Dec. 28; 364(4): 801-807).

COL1a1: Procollagen Type I, Alpha 1

In steatohepatitis model rats induced by feeding diabetes model rats with methionine-deficient, choline-deficient diet, suppression of liver fibrosis, activity of stellate cell, and expression of fibrosis gene (TGF-β, alpha 1[I] procollagen, etc.) by olmesartan (an angiotensin II type 1 receptor blocker) has been reported (Eur J. Pharmacol. 2008 Jul. 7; 588(2-3): 316-324).

Complement Factor D: Adipsin

Complement factor D is a serine protease which is necessary for initiation of the complement activation and which factor is secreted from adipocytes into the blood. Serum concentration of the complement factor D is regulated by catabolism in kidney, and patients suffering from kidney diseases exhibit increased level of complement factor D.

Hepatocyte-specific Pten knockout mouse experiences steatohepatitis and liver carcinogenesis, and RT-PCT of the hepatocytes revealed induction of adipocyte-specific gene (adipsin, adiponectin, etc.) (Watanabe et al., Hepatology October 2004 428A 609).

In the present invention, we have for the first time confirmed the increase of the complement factor D in the plasma from the NAFLD patients. This indicates that the complement factor D can be a marker measurable in blood.

TNFR (Tumor Necrosis Factor Receptor) Superfamily, Member 19 (TAJ)

Members of tumor necrosis factor receptor superfamily are type I membrane proteins, and their extracellular domain exhibits high homology.

TNFAIP (Tumor Necrosis Factor Alpha Induced Protein) 6

TNFAIP6 protein is a cleavable signal peptide comprising 277 amino acids.

Its expression is activated by TNFα, IL-1, and lipopolysaccharide in fibroblast, peripheral blood mononuclear cell, synoviocyte, and chondrocyte.

VLDLR: Very Low Density Lipoprotein Receptor

VLDLR is a protein comprising 846 amino acids. VLDLR is constituted from 5 domains, and has a signal peptide comprising 27 residues. The gene of the VLDLR expressed in heart, muscle, and adipose tissue is activated by fatty acid metabolism.

Lipoprotein Lipase

Lipoprotein lipase is an enzyme which hydrolyzes triglyceride mainly in chylomicron and VLDL into glycerol and fatty acid.

Ear (Eosinophil Associated Ribonuclease) A Family, Members 1, 2, 3, and 12

These are members of ribonuclease (RNAse) family.

INSL5: Insulin Like 5

INSL5 is a hormone of insulin gene superfamily, which is estimated to be a protein comprising 135 amino acids. INSL5 regulates cell growth, metabolism, and tissue-specific function, and this family member is characterized by signal peptide.

TGF β2: Transforming Growth Factor Beta 2

Transforming growth factor beta (TGF-β) controls propagation, cell differentiation, and other functions in various types of cells, and TGF-β plays various roles in immunosystem, cancer, heart disease, and diabetes. TGF-β functions as an antiproliferative factor in normal epithelial cell and in the early stages of tumorigenesis. Some cells secrete TGF-β and have a receptor for the TGF-β. TGF-β is a secretory protein having three isoforms TGF-β1, TGF-β2, and TGF-β3.

HAMP: Hepcidin Antimicrobial Peptide 1

HAMP is an anti-bacterial and anti-fungal protein expressed in liver. RAMP is also a signal molecule in the iron metabolysis. RAMP circulates in blood, and inhibits iron absorption in small intestine when iron is excessively supplied in the body.

Lipase H: Lipase Member H (LIPH)

Lipase H is a member of triglyceride lipase family, and it is a protein comprising 451 amino acids. Lipase H protein is a secretory protein having a molecular weight of about 63 kDa. Lipase H has been indicated to relate with lipid and energy metabolism like other members of lipase.

CYP7B1: Cytochrome P450, Family 7, Subfamily b, Polypeptide 1

Synthesis of bile acid from cholesterol takes place by way of two paths: neutral pathway involving cholesterol 7-alpha-hydroxylase (CYP7A1) and acidic pathway involving microsome oxysterol 7-alpha-hydroxylase (CYP7B1).

In CYP7B1 knockout mouse, increase in the level of 2 oxysterols, namely, 25-hydroxycholesterol and 27-hydroxycholesterol in the serum and tissue has been reported.

Of the second factor group, the markers which are preferable for the NASH detection and diagnosis as well as evaluation of seriousness of or therapeutic effects on the NASH include IL-2, apolipoprotein A-IV, CCL2, thrombospondin 1, trehalase, MMP12, MMP13, TIMP1, complement factor D, apolipoprotein C-II, lipoprotein lipase, HAMP, and lipase H in view of the convenience of the measurement. These markers are particularly useful in evaluating the therapeutic effects of the NASH treatment by a pharmaceutical composition containing at least one member selected from EPAs as its effective component. Among these, the particularly preferred are apolipoprotein A-IV, thrombospondin 1, trehalase, complement factor D, apolipoprotein C-II, and lipase H, and the most preferred are thrombospondin 1 and complement factor D.

Biological Specimen

The biological specimen used the present invention is not particularly limited, and exemplary specimens include blood, plasma, serum, urine, body fluid, tissue, and the like collected from the subject. The preferred are blood, plasma, and serum. Collection of the biological specimen from the subject may be accomplished by a method known in the art.

Measurement of the Marker

The "amount" when the marker factor of the present invention is a protein is not particularly limited, and the "amount" measured may be absolute amount or concentration of the marker in the blood specimen.

In the present invention, an antigen recognized by the corresponding antibody may be used as a marker. As long as it is an antigen which can be recognized and measured by the corresponding antibody, the marker of the present invention may be a partial sequence of the amino acid sequence of the target marker, namely, a part of the marker protein, or the one having altered conformation or the one modified by sugar chain or lipid addition.

The specific method used for the measurement is not particularly limited, while the preferred is use of an immunoassay. Both competitive methods and non-competitive methods (such as sandwich method) may be used, and exemplary methods include enzyme-linked immunoassay, enzyme-linked immunosorbent assay (ELISA), EIA, radioimmunoassay (RIA), fluoroimmunoassay (FIA), and luminescence immunoassay (LIA). Also applicable are aggregation, western blotting, and method using a protein chip. The measurement may also be accomplished by a method using proteomics, and the method is not limited to those as described above. In addition, a commercially available assay kit may be used in the measurement.

When the marker used in the present invention is a protein, the evaluation may be conducted by measuring the "activity". The method used for measuring the "activity" of the marker of the present invention is not particularly limited, and in an exemplary method, the protein activity may be determined by reacting the marker protein with a substrate of the protein for a predetermined period, and determining amount of the resulting substance or other secondarily produced substance.

Antibody Used for the Marker Assay

The antibody used for the protein detection is not particularly limited for its type or source as long as it can undergo specific binding to the particular protein. The antibody used is either a monoclonal antibody or a polyclonal antibody, and preferably, a monoclonal antibody.

Antibody Preparation

The method used for the antibody preparation is not particularly limited, and a monoclonal or polyclonal antibody may be used by sensitizing an animal with the target protein or a peptide having its partial sequence. A monoclonal antibody may be prepared, for example, by fusing an antibody producing cell with a myeloma cell to produce a hybridoma having autonomous proliferative capacity, screening the clone producing the antibody having the target specificity, cultivating the screened cell, and purifying the secreted antibody. A polyclonal antibody may be prepared by collecting serum of the animal and purifying the collected serum. Other methods of the preparation include phage display method.

Method Used for Measuring the Marker Gene

When the marker of the present invention is a gene, the gene may be a DNA such as cDNA or an RNA such as mRNA. The method used for measuring the amount of gene expression is not particularly limited, and exemplary methods include those using a microarray, real time PCR, Southern blotting, Northern blotting, in situ hybridization, and dot plotting. The biological specimen used in such a case is preferably a tissue, and in particular, a liver tissue.

2. Method for Detecting NASH or Evaluating Seriousness of or Therapeutic Effects on NASH In the present invention, detection or diagnosis of NASH and evaluation of seriousness of or therapeutic effects on the NASH may be simply referred to as "evaluation". The inventive method used for the evaluation of the NASH is a method for providing an index which physicians can use in diagnosing the NASH or in evaluating seriousness of or therapeutic effects on the NASH.

The method for NASH detection or evaluating the seriousness of or therapeutic effects on the NASH of the present invention employs at least the first factor as described above.

<Method for Detecting NASH>

The method for detecting NASH of the subject according to the present invention is a method including the step of A) measuring amount and/or activity of at least one first factor in the biological specimen from the subject. This method may further comprise the step of measuring amount and/or activity of at least one second factor, and preferably, this method further comprises the step of B) preliminarily determining cut off value, which is the borderline between the positive and negative of the disease, with respect to the target marker and comparing the measurement of the subject obtained in the A) with the thus determined cut off value. In this case, suffering of the subject from the NASH is indicated when the measurement of the subject is positive in comparison with the cut off value.

In the present invention, the method used for determining the cut off value is not particularly limited, and exemplary cut off values may include average of the healthy subjects±2SD (standard deviation), the average of the healthy subjects±1SD, the average of the healthy subjects±3SD, and average of the healthy subjects. The cut off value, however, is preferably the average of the healthy subjects±2SD.

In an exemplary embodiment using the first factor described in Example 1 of the present invention, when the cut off value is determined by using average+2SD, the cut off value is 652 (pg/mL) in the case of IL-1ra, and in this case, sensitivity is 100% and specificity is 100%. Similarly, when the cut off value is determined by using average+2SD, the cut off value is 17.2 (pg/mL) in the case of sCD40, and in this case, sensitivity is 100% and specificity is 90%. The cut off value of HMGB1 is calculated to be 3.4 (ng/mL), with the sensitivity of 86% and the specificity of 100%.

Alternatively, the cut off value may be determined by using Roc curve. In an exemplary embodiment using the Roc curve, the biological specimens of healthy subjects and NASH patients are measured for the target markers, and sensitivity (positive rate), specificity, and pseudopositive rate (1-specificity) for each measurement are determined to thereby depict the Roc curve by plotting pseudopositive rate (1-specificity) in the X axis and sensitivity (positive rate) in the Y axis. When the marker is an ideal marker having excellent sensitivity and specificity, its Roc curve will approach upper left corner of the quadrant, and the value of the point with minimum distance to the upper left corner may be used for the cut off value. The cut off value may also be determined by using a method using Youden index.

When NASH is detected by using a cut off value, the cut off value will be different by the definition of the NASH as well as the method used in measuring the marker. Accordingly, the cut off value is preferably determined by preliminarily confirming the measurements of the healthy subjects and the NASH patients for the target marker, and the detection is conducted by using the thus determined cut off value. When marker is measured by using plasma collected from the subject by the procedure according to Examples of the present invention, the NASH detection may be conducted by referring to the values obtained in the Examples of the present invention.

<Method Used for Evaluating Seriousness of NASH>

The method for evaluating seriousness of the NASH in the subject according to the present invention is a method used for evaluating NASH seriousness of the subject, at least comprising the step of A) measuring amount and/or activity of at least one first factor in the biological specimen from the subject. This method may further comprise the step of measuring amount and/or activity of at least one second factor.

As in the case of the NASH detection method as described above, the method may further comprise the step of preliminarily determining a cut off value, and comparing the measurement obtained in A) with the cut off value. The method may also comprise the step of comparing the time course of the measurement of the marker (factor) in the biological specimen from the subject.

In such method, the NASH is indicated to be less serious when the marker measurement of the subject is closer to the average of the healthy subjects. In contrast, seriousness of the NASH or worsening of the pathological conditions is indicated when the marker measurement of the subject is less close to the average value of the healthy subjects.

<Method for Evaluating Therapeutic Effects>

The method for evaluating therapeutic effects on the NASH in the subject according to the present invention is a method used in evaluating the therapeutic effects when the NASH subject is treated, and the method at least comprises the step of measuring at least one factor selected from the group consisting of first factor group and second factor group as a marker in the biological specimen from the subject at least twice at a particular interval, and comparing the measurements.

In this step, at least one factor selected at least from the first factor group is preferably used for the marker. An embodiment wherein the marker is measured two ore more times at a certain time interval to compare the time course of marker measurement is also preferable. As in the embodiment as described above, the method may further comprise the step of comparing the marker measurement of the subject with the cut off value.

The NASH treatment in the present invention includes administration of the NASH therapeutic agent, exercise therapy, diet therapy, and other therapeutic methods conducted for the purpose of treating the NASH such as phlebotomy and surgical treatment. In the present invention, the period in which the NASH is treated is referred to as the NASH treatment period.

In this method for evaluating the therapeutic effects, the NASH therapeutic effects are demonstrated when the marker measurement of the subject becomes closer to the average value of the healthy subjects. On the contrary, absence of the NASH therapeutic effects is indicated when the marker measurement of the subject deviates from the average value of the healthy subjects.

The method for evaluating the therapeutic effects of the present invention is preferably conducted by continuing the treatment of NASH for a certain period, and conducting the measurement of the marker at a certain interval during the NASH treating period. In the present invention, "certain interval" is not particularly limited. However, the period is preferably 1 week, more preferably 1 month, 3 months, 6 months, or 1 year, or alternatively, at least 1 year. Also preferred is an embodiment wherein the marker (factor) in the biological specimen from the subject is periodically measured at an interval of, for example, 3 months.

When a NASH therapeutic agent is administered for the treatment of the NASH, and the evaluation of the therapeutic effects of the NASH therapeutic agent is conducted, the NASH therapeutic agent used is not particularly limited, and it may be the same as those described below for the NASH therapeutic method. However, the preferred is the pharmaceutical composition containing at least one member selected from EPAs as its effective component.

When the NASH therapeutic agent used is a pharmaceutical composition containing at least one member selected from EPAs as its effective component, the method for evaluating the therapeutic effects on the NASH is preferably conducted by using the marker of the second factor.

Accordingly, the method according to this aspect of the present invention is a method for evaluating therapeutic effects of the pharmaceutical composition containing at least one member selected from EPAs as its effective component in the subject comprising the steps of
a) measuring the level of at least one member selected from the second factor group in the biological specimen from the subject (first measurement),
b) administering the pharmaceutical composition containing at least one member selected from EPAs as its effective component,
c) measuring the value of the factor measured in the step a) in the biological specimen from the subject (second measurement), and
d) comparing the first measurement and the second measurement of the subject to thereby evaluate conditions of the subject.

<Evaluation by a Combination of Markers>

The marker of the present invention may be used alone. Alternatively, two or more markers may be used in combination to improve precision of the NASH detection or evaluation. The marker typically includes at least the first factor.

For example, when two types of markers according to the present invention are used in the detection of the NASH, the NASH may be determined to be present in the subject when both two markers are positive. When only one marker is positive, other marker of the present invention may be additionally measured, or alternatively, the test results may be combined with additional diagnosis method to indicate the presence of NASH.

Preferable embodiments of the combined use of the markers of the present invention are not particularly limited. However, a preferred combination includes an IL-1 receptor antagonist as a marker used for detection of the NASH as well as evaluation of the seriousness of and therapeutic effects on the NASH, and combination of sCD40 which is said to be relevant with apoptosis and HMGB1 which is said to be relevant with necrosis is also preferable. Since sCD40 and HMGB1 tend to correlate with AST, the embodiment using this combination for the evaluation of seriousness and therapeutic effects is also preferable.

The marker of the present invention may also be used by combining with the test, blood test marker, test by imaging (ultrasound, CT, MRI, etc.), or index of therapeutic effects which is conventionally used for diagnosing and evaluating the NASH. In the present invention, such tests and indexes are generally referred to as additional test index.

The marker of the present invention may also be used by combining with diagnosing method. Detection and evaluation precision may be improved by combining with two or more methods.

Examples of the non-limiting conventional indexes used for the NASH detection and evaluation include serum lipid data (TG, LDL, HDL, TC, VLDL, EPA concentration, EPA/ arachidonic acid (AA) ratio, etc.), free fatty acid, obesity, AST, ALT, AST/ALT ratio, serum ferritin, serum thioredoxin, malondialdehyde, 4-hydroxynonenal, nitric oxide, HOMA-IR, platelet count, TNFα, adiponectin, leptin, high sensitivity CRP, hyaluronic acid, type IV collagen 7S, procollagen III polypeptide, CK18 fragment, pathological findings (steatosis, hepatocellular ballooning, lobular inflammation, ballooning inflammation, ballooning degeneration, fibrosis, Mallory body), NAS score (Kleiner et al., Hepatology 2005; 41: 1313-1321), Fas (Gastroenterology 2003; 125(2) 437-43), HbA1c, fasting glucose, body weight, and waist circumference.

For example, evaluation by the combination of sCD40, HMGB1, and complement factor D which are the markers of the present invention with NAS score and ALT which are the additional test index is also preferable. Also preferred is the evaluation by the combination of HMGB1 which is the marker of the present invention with Fas which is the additional test index.

Use of fatty acid content in blood or liver and compositional ratio of the fatty acids for the index of the therapeutic effects on the NASH is also preferable. Fatty acids may be measured by a method known in the art such as measurement of 24 fractions to calculate content of each fatty acid in % by mole in the entire fatty acid. Exemplary non-limiting compositional ratios of the fatty acids that can be used include oleic acid (OA)/stearic acid (SA) ratio, stearic acid (SA)/palmitic acid (PA) ratio, and oleic acid (OA)/palmitic acid (PA) ratio (see WO 2009/151125).

3. Therapeutic Method

The present invention provides a method for treating NASH comprising the steps of evaluating a subject by the method for detecting the NASH and/or the method for evaluating the seriousness of the NASH as described above, and treating the subject. In the present invention, the NASH treatment is preferably administration of a NASH therapeutic agent, and more preferably, administration of a pharmaceutical composition containing at least one member selected from EPAs as its effective component. The therapeutic method also includes a method wherein NASH is treated while evaluating the therapeutic effects of the NASH therapeutic agent by using the marker of the present invention.

<Nash Therapeutic Agent>

The NASH therapeutic agent used in the therapeutic method of the present invention is not particularly limited as long as it is a drug used for treating, ameliorating, or alleviating the pathological conditions of the NASH, and exemplary NASH therapeutic agents include the pharmaceutical composition containing at least one member selected from EPAs as its effective component as will be described below, thiazolidine derivatives (pioglitazone, rosiglitazone, etc.), biguanide (metformin, etc.), a glucosidase inhibitor, sulfonyl urea, nateglinide, DPP-4 inhibitor (sitagliptin, alogliptin, vildagliptin, saxagliptin, linagliptin, etc.), GLP-1 receptor agonist (liraglutide, exenatide, taspoglutide, etc.), PDE-4 inhibitor, fibrate (bezafibrate, etc.), HMG-CoA reductase inhibitor (pravastatin, atorvastatin, etc.), probucol, angiotensin II-1 type receptor antagonist (ARB: losartan, etc.), ursodeoxycholic acid, taurine, polyenephosphatidylcholine, antioxidant (vitamine E, vitamin C, nicotinic acid tocopherol, N-acetylcysteine, etc.), anti-TNF therapy (anti-TNFα antibody, etc.), pentoxifylline, S-adenosylmethionine, milk thistle, and probiotics. The NASH therapeutic agent is administered at a therapeutically effective amount. These drugs may also be administered in combination with the pharmaceutical composition containing at least one member selected from EPAs as its effective component, and such combined administration may realize excellent therapeutic effects. In the case of the NASH patient suffering from diabetes, combined use of a pharmaceutical composition containing at least one member selected from EPAs as its effective component and an antidiabetic agent (for example, pioglitazone, sulfonyl urea, DPP-4 inhibitor, etc.) is preferable. Administration of the drug which has been taken by the subject (for example, hypotensive agent, antilipemic agent, antithrombotic agent, etc.) is preferably continued. For example, an antithrombotic agent such as warfarin or clopidogrel may be administered in combination with the pharmaceutical composition containing at least one member selected from EPAs as its effective component.

<Pharmaceutical Composition Containing at Least One Member Selected from EPAs as its Effective Component>

The EPAs used in the present invention may be a commercially available product, or the one produced by purifying a fish oil or EPA-producing bacteria or its culture medium by a method known in the art such as continuous distillation, urea addition, liquid chromatography, supercritical fluid chromatography, or a combination thereof followed by optional esterification to produce an ester such as an alkyl ester such as ethyl ester or glyceride. The EPAs used may also be a salt with an inorganic base such as sodium salt or potassium salt, a salt with an organic base such as benzylamine salt or diethylamine salt, or a salt with a basic amino acid such as arginine salt or lysine salt.

In the present invention, the EPAs include free EPA as well as salts and esters as described above unless otherwise noted. When administered to a human or an animal, the EPAs are preferably those which are pharmaceutically acceptable, and among these, the preferred EPA is EPA-E in ester form.

The pharmaceutical composition containing at least member selected from EPAs as its effective component that is used in the present invention may contain pure EPAs or EPAs in combination with other fatty acid as its effective component. Exemplary such fatty acids other the EPAs include unsaturated fatty acids such as docosahexaenoic acid, docosapentaenoic acid, docosamonoenoic acid, arachidonic acid, icosatetraenoic acid, icosatrienoic acid, icosamonoenoic acid ocatadecatetraenoic acid, α-linolenic acid, linoleic acid, oleic acid, palmitoleic acid, hexadecatetraenoic acid, hexadecatrienoic acid, and hexadecadienoic acid; and saturated fatty acids such as behenic acid, arachidic acid, stearic acid, palmitic acid, and myristic acid. The fatty acid as mentioned above may be in its free form, a salt with an inorganic base such as sodium salt, a salt with an organic base such as benzylamine salt, or an ester such as an alkyl ester, for example, ethyl ester or a glyceride.

When the pharmaceutical composition containing at least one member selected from EPAs as its effective component of the present invention contains a fatty acid other than the EPAs as its effective component, the composition preferably contains the EPAs at an amount of at least 50% by weight, more preferably at least 70% by weight, still more preferably at least 85% by weight, still more preferably at least 90% by weight, and most preferably at least 96.5% by weight of the entire fatty acid. Preferably, arachidonic acid is contained at a minimum amount.

When EPA-E and DHA-E are used, compositional ratio of the EPA-E/DHA-E and content of the EPA-E+DHA-E in the entire fatty acid are not particularly limited. However, the compositional ratio of EPA-E/DHA-E is preferably at least 0.8, more preferably at least 1.0, and still more preferably at least 1.2. EPA-E+DHA-E is preferably the one having a high purity, for example, the one having content of the (EPA-E+DHA-E) in the entire fatty acid and its derivatives of at least 40% by weight, more preferably at least 55% by weight, and still more preferably at least 84% by weight, and most preferably at least 96.5% by weight. Preferably, other long chain saturated fatty acid is included at lower content, and among long chain unsaturated fatty acid, ω6 fatty acid, and in particular, arachidonic acid is preferably included at lower content of less than 2% by weight, more preferably less than 1% by weight.

The pharmaceutical composition containing at least one member selected from EPAs as its effective component of the present invention may further contain optional components such as excipient, binder, lubricant, colorant, flavor, sterilized water, vegetable oil, harmless organic solvent, harmless solubilizing agent (such as glycerin and propylene glycol), emulsifier, suspending agent (for example, Tween 80 and gum arabic solution), isotonic agent, pH adjusting agent, stabilizer, and soothing agent.

Since EPAs are highly unsaturated, the preparation as described above preferably contains an antioxidant at an amount effective for suppressing oxidation of the EPAs. Exemplary antioxidants include butylated hydroxytoluene (BHT), butylated hydroxyanisole (BHA), propyl gallate, gallic acid, pharmaceutically acceptable quinone, and α-tocopherol.

Exemplary dosage forms of the preparation include tablet, capsule, microcapsule, granules, fine granules, powder, oral liquid preparation, suppository, syrup, inhalant, eye drops, ointment, injection (emulsion, suspension, and non-aqueous), and solid for injection which is emulsified or suspended immediately before use.

An exemplary soft capsule containing EPA-E is a commercially available soft capsule containing high purity EPA-E which is domestically sold in the product name of Epadel and Epadel S (both manufactured by Mochida Pharmaceutical Co., Ltd.) as a safe therapeutic agent for arteriosclerosis obliterans and hyperlipidemia exhibiting reduced side effect expression. An exemplary mixture of the EPA-E and the DHA-E is Lovaza (GlaxoSmithKline; a soft capsule containing about 46.5% by weight of EPA-E and about 37.5% by weight of DHA-E) which is commercially available in the U.S. as a therapeutic agent for hypertriglycemia.

The pharmaceutical composition containing at least one member selected from EPAs as its effective component of the present invention is used at an amount sufficient for expressing the target effect. The amount, however, may be adequately adjusted depending on the composition's dosage form, administration route, and daily administration frequency, seriousness of the symptoms, body weight, age, and the like.

In the case of oral application, the pharmaceutical composition is administered at 0.1 to 9 g/day, preferably 0.5 to 6 g/day, and more preferably 1 to 3 g/day in terms of EPA in 3 divided dose. If necessary, entire dose may be administered at once/day, or in several divided doses/day. The pharmaceutical composition may also be administered at 0.1 to 10 g/day, preferably 0.3 to 6 g/day, more preferably 0.6 to 4 g/day, and still more preferably 0.9 to 2.7 g/day or 0.9 to 1.8 g/day in terms of EPA-E and/or DHA-E.

<Method for Treating Nash Including the Method for Evaluating Therapeutic Effects of the Present Invention>

It is also preferable that the therapeutic method for NASH of the present invention includes the method for evaluating therapeutic effects on NASH as described above in its procedure. More specifically, the present invention also provides, as another embodiment of the present invention, a therapeutic method for NASH comprising the steps of measuring at least one marker selected from the group consisting of the first factor group and the second factor group as the marker in the biological specimen of the subject at last twice at a certain interval, and comparing the measurements to evaluate the therapeutic effects on the NASH. This therapeutic method may further comprise the step of determining therapeutic method of the subject based on the evaluation of the therapeutic effects. For example, in the case of subjects with the evaluation results of no or insufficient therapeutic effects of the NASH therapeutic agent, increase in the dose of the therapeutic agent, addition of therapeutic method or agent, or change of the therapeutic method or agent may be conducted.

On the other hand, in the case of the subjects with the evaluation results of sufficient therapeutic effects, continuation of the same therapeutic agent is desirable.

In the therapeutic method for NASH of the present invention, the particularly preferable therapeutic agent is a pharmaceutical composition containing at least one member selected from EPAs as its effective component, and in this case, the marker used for the evaluation of therapeutic effects is preferably the second factor.

<Method for Treating NASH Including the Selection of Therapeutic Method by the Marker of the Present Invention>

The therapeutic method for NASH of the present invention is a method comprising the steps of measuring the biological specimen from the subject by using at least one factor selected from the group consisting of first factor group and second factor group for the marker of the present invention, selecting the NASH therapeutic method using EPAs based on the evaluation of the measurement, and administering the subject with a pharmaceutical composition containing EPAs. More specifically, high therapeutic effects by the EPAs are likely to be attained in the subject with marked abnormality of the second factor group since the factors of the second factor group have been confirmed to be highly relevant with the effects of the EPA-E.

The marker which is preferable for selecting the therapy using the EPAs is the marker selected from the second factor group, and the more preferred are thrombospondin 1 and complement factor D. sCD40 and HMGB1 are also preferable as the marker for selecting the treatment using EPAs. These markers may be used in combination with additional test index.

For example, when the complement factor D which is the factor of the second factor group is measured in the subject and the measurement is higher than the preliminarily determined reference value, the subject desirably undergoes a treatment using a pharmaceutical composition containing EPAs. In the case of the subject who has been measured to have measurements of complement factor D, sCD40, and HMGB1 higher than the preliminarily determined reference values, the subject desirably undergoes a treatment using a pharmaceutical composition containing EPAs. The method used for determining the reference value is not particularly limited, and the medical professionals can determine an adequate value based on average of the particular factor in the healthy subjects, NAFLD patients, and NASH patients. The therapeutic method to be employed may also be determined using a combination of the inventive marker with an additional test index (NAS score, ALT value or EPA/AA ratio, for instance).

In other words, this method is a NASH therapeutic method comprising the steps of selecting subjects who are suitable for the treatment of administering EPAs from the NASH and/or NAFLD subjects by using the marker of the present invention, and administering such subjects with a pharmaceutical composition containing the EPAs.

4. Kit

The present invention provides a kit used for NASH detection or evaluation of the seriousness of or therapeutic effects on the NASH. The kit measures amount and/or activity of at least one member selected from the group consisting of first factors and second factors, and preferably, at least one member selected from the first factor group in the biological specimen from the subject.

The assay kit when the marker of the present invention is a protein is not particularly limited as long as it includes means for measuring such marker. However, the assay kit preferably contains an antibody against the marker. The antibody against the protein may also be an antibody fragment, and the antibody preferably contains a marked antibody. Preferred is use of a sandwich assay kit.

The assay kit used in measuring activity of a protein as the marker of the present invention includes a substrate which is specific for the protein. When sPLA2 activity is measured as the marker of the present invention, the substrate used for measuring the sPLA2 activity is not particularly limited, and the substrate preferably contains a phospholipid since PLA2 is an enzyme which hydrolyzes the phospholipid at sn-2 position. An exemplary such substrate is diheptanoyl thiophosphatidylcholine.

Preferably, the assay kit of the present invention may also contain a reference standard or a color-producing reagent for the protein.

Next, the present invention is described in detail by referring to Examples, which by no means limit the scope of the present invention.

EXAMPLES

Example 1

Confirmation Test of Human NASH Patient

Concentration as the amount of antigen of IL-1ra, sCD40, HMGB1, and sPLA2 group IIA as well as sPLA2 activity of plasma (7 specimens) from human NASH patients who have been diagnosed as having NASH by liver biopsy and plasma (10 specimens) from healthy subjects were measured and compared.

The measurement was conducted by using commercially available assay kits, namely, IL-1ra (Catalog No.: DRA00B; R&D Systems Inc., US), sCD40 (KT-003; KAMIYA BIOMEDICAL COMPANY, Seattle, Wash.), HMGB1 (326054329; Shino-Test Corporation, Japan), sPLA2 group IIA (585000; Cayman Chemical Company, US), and sPLA2 activity (765001; Cayman Chemical Company, US).

More specifically, IL-1ra was measured by (1) adding the specimen to a microplate having anti IL-1ra monoclonal antibody immobilized thereon to allow the reaction to proceed, and then, (2) adding a labeled polyclonal antibody for the reaction to proceed. Similarly, sCD40 was measured by using (1) an anti-sCD40 monoclonal antibody and (2) a labeled polyclonal antibody, and HMGB1 was measured by using (1) an anti-HMGB1 polyclonal antibody and (2) a labeled anti-HMGB1,2 monoclonal antibody. sPLA2 group IIA was measured by using (1) an anti-sPLA2 group IIA monoclonal antibody, and adding acetylcholine esterase:Fab' complex which selectively reacts with different epitopes of the sPLA2 molecule, and then adding the specimen to promote the reaction. sPLA2 activity was measured by using diheptanoyl thiophosphatidylcholine for the substrate, and allowing the substrate to react with the specimen to thereby enable detection of the resulting free thiols by DTNB.

The results of the measurement are shown in Table 1. The measurements are shown as average (mean)±standard deviation (SD). Significant difference was tested by Wilcoxon test, and the results of the Wilcoxon test (healthy subjects vs NASH patients) are shown according to the criteria: +($p<0.05$) and ++($p<0.01$).

TABLE 1

| Factor | Healthy subject (Mean ± SD) | NASH (Mean ± SD) | Wilcoxon test |
|---|---|---|---|
| IL-1ra (pg/mL) | 450 ± 101 | 3366 ± 3670 | ++ |
| sCD40 (pg/mL) | 3.8 ± 6.7 | 147.0 ± 78 | ++ |
| HMGB1 (ng/mL) | 1.0 ± 1.2 | 38.8 ± 25.5 | ++ |
| sPLA2 group IIA (pg/mL) | 4526 ± 1728 | 32855 ± 53387 | + |
| sPLA2 activity (nmol/min/mL) | 4.6 ± 0.3 | 4.4 ± 3.3 | + |

Concentration of the IL-1ra, sCD40, HMGB1, and sPLA2 group IIA in the plasma of the NASH patients significantly increased compared to the healthy subjects. On the other hand, the sPLA2 activity in the plasma of the NASH patients significantly decreased compared to the healthy subjects. The reason for the simultaneous increase in the sPLA2 group IIA concentration in the NASH patient plasma with the decrease in the sPLA2 activity is not certain. Such result may have been obtained since not the activity of only the sPLA2 group IIA but that of the entire sPLA2 was measured as the sPLA2 activity. Alternatively, such result may have been caused by increase of the sPLA2 group IIA without activity that was also measured with the sPLA2 group IIA antibody.

Figure 2:
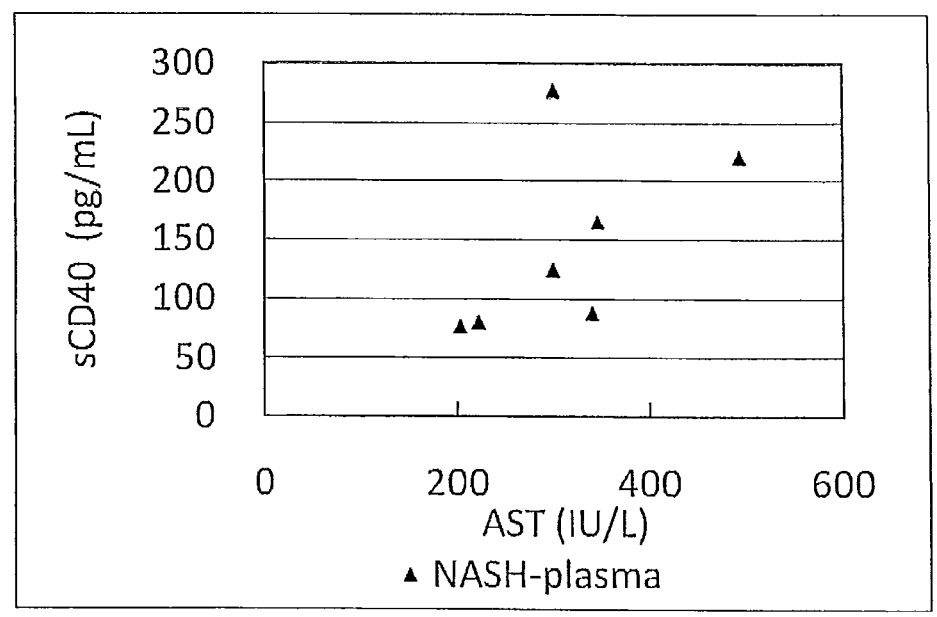
FIG. 2 is a graph showing sCD40 value in plasma in relation to plasma AST value of the NASH patients.
Figure 3:
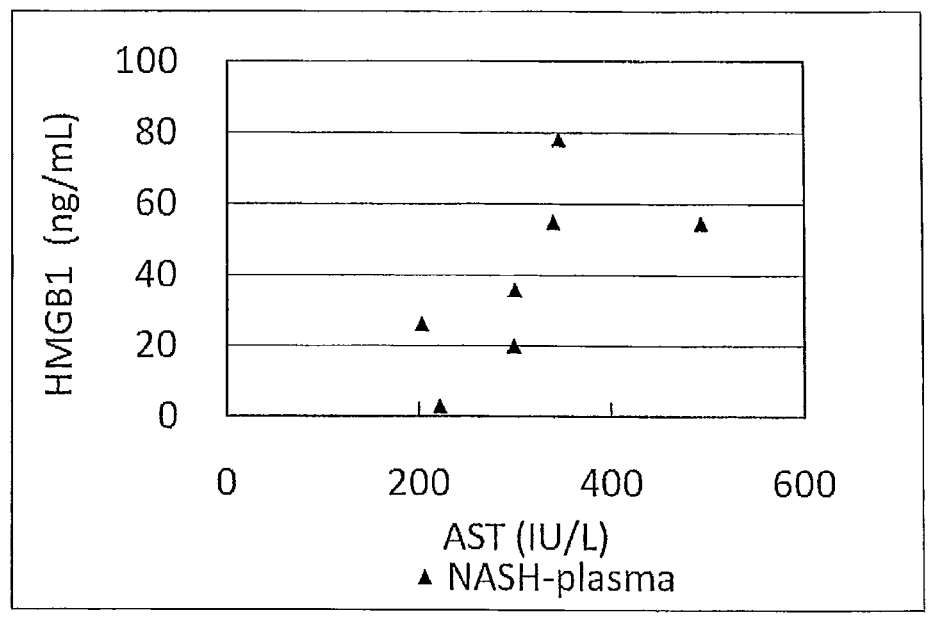
FIG. 3 is a graph showing HMGB1 value in plasma in relation to plasma AST value of the NASH patients.
Figure 4:
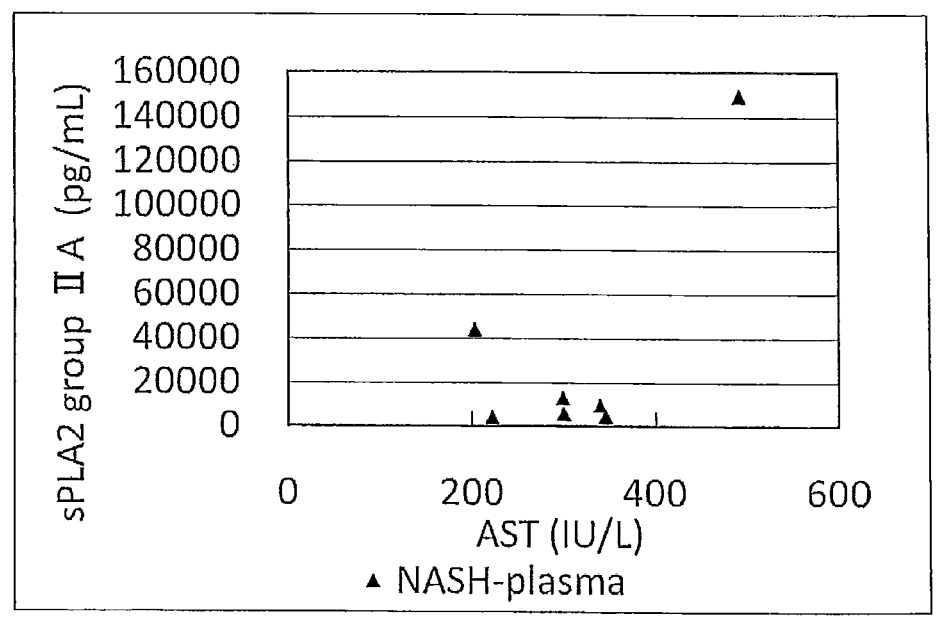
FIG. 4 is a graph showing sPLA2 group IIA value in plasma in relation to plasma AST value of the NASH patients.
Figure 5:
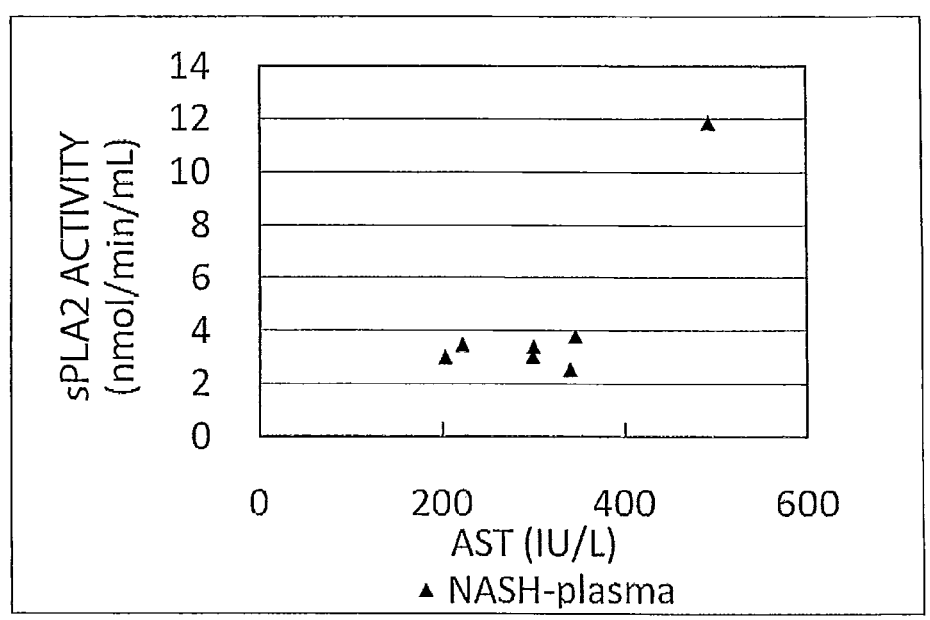
FIG. 5 is a graph showing sPLA2 activity value in plasma in relation to plasma AST value of the NASH patients.

Correlation between the value of these factors and the AST value in the NASH patients is shown in FIG. 1 (IL-1ra), FIG. 2 (sCD40), FIG. 3 (HMGB1), FIG. 4 (sPLA2 group IIA), and FIG. 5 (sPLA2 activity). In all these factors, the value tended to correlate with the AST value, and this tendency was particularly strong in HMGB1 and sCD40.

The results as described above indicated that these factors could be used as a marker for detecting NASH or evaluating seriousness of the NASH, and/or a marker for determining the therapeutic effects of the NASH therapeutic agent.

Example 2

Selection of Candidates for the Second Marker

B6 mice (10 week old) were divided into control group (I), HF-HS group (II), and EPA group (III) (n=7 to 10), and the mice were raised for 20 weeks by free feeding of the following diet.

Group I: normal diet (F-1 without fish meal) (manufactured by Funabashi Farm)

Group II: high fat/high sugar diet (Harlan Laboratories)+ 5% ethyl palmitate (Wako Pure Chemical Industries)

Group III: high fat/high sugar diet (Harlan Laboratories)+ 5% EPA-E (Nippon Suisan Kaisha, Ltd.)

After raising for 20 weeks, fatty liver was observed in the group II, while the fatty liver was not observed in the groups I and III.

Liver was extirpated from the mice of each group, and RNA was extracted by homogenization to conduct gene microarray analysis of the liver. The genes were selected as described below.

(1) Genes with group II/group I expression ratio of 2 or higher and group III/group II expression ratio of up to 1/2 were selected.

(2) Genes with the group II/group I expression ratio of up to 1/2 and the group III/group II ratio of 2 or more were selected.

(3) Genes exhibiting non-significant expression for all of groups I, II, and III were selected.

(4) Genes which are (1) but not (3) were selected.

(5) Genes which are (2) but not (3) were selected.

(6) Selection of candidates for the second marker (A)

Next, factors with the possibility of protein secretion into blood were selected from the genes (4), and then, genes satisfying any of relevance with lipid metabolism, relevance with inflammation, increase of expression in the liver of SREBP transgenic mouse were selected from these genes. The thus obtained gene group (second factor (A) group) is shown in Table 2.

TABLE 2

| Second factor (A) group |
|---|
| Interleukin 2 |
| Apolipoprotein A-IV |
| Chemokine (C-C motif) ligand 2 (CCL2) |
| Thrombospondin 1 |
| Interleukin 3 receptor, alpha chain |
| Lymphocyte antigen 6 complex, locus D |
| Matrix metallopeptidase 12 |
| Trehalase (brush-border membrane glycoprotein) |
| Matrix metallopeptidase 13 |
| Tissue inhibitor of metalloproteinase 1 |
| Procollagen, type I, alpha 1 |
| Complement factor D |
| Apolipoprotein C-II |
| Tumor necrosis factor receptor superfamily, member 19 |
| Very low density lipoprotein receptor |
| Tumor necrosis factor alpha induced protein 6 |
| Eosinophil-associated, ribonuclease A family, member 1 |
| Eosinophil-associated, ribonuclease A family, member 2 |
| Eosinophil-associated, ribonuclease A family, member 3 |
| Eosinophil-associated, ribonuclease A family, member 12 |
| Lipoprotein lipase |

(7) Extraction of Candidates for the Second Marker (B)

Genes were selected from the genes (5) by conducting the procedure corresponding to (6). The thus obtained gene group (second factor (B) group) is shown in Table 3.

TABLE 3

| Second factor (B) group |
|---|
| Insulin-like 5 |
| Transforming growth factor, beta 2 |
| Hepcidin antimicrobial peptide 1 |
| Lipase, member H |
| Cytochrome P450, family 7, subfamily b, polypeptide 1 |

Example 3

Confirmation Test of Use of Second Factor on Human NAFLD Patients

Plasma concentration of each of factors described in Tables 2 and 3 is measured in human NAFLD patients and healthy subjects. The measurement may be conducted by using a commercially available assay kit or by using the corresponding antibody. If unavailable, the corresponding antibody may be prepared by the procedure as described above.

Concentration of thrombospondin 1 and complement factor D of Group (A) (Table 2) was measured for the plasma (3 specimens) from human NAFLD patients (excluding human NASH patients who have been diagnosed as having NASH by liver biopsy) and the plasma (10 specimens) from healthy subjects.

The measurement was conducted by using commercially available assay kits, namely, thrombospondin 1 (Catalog No.:

DTSP10; R&D Systems Inc., US) and complement factor D (DFD00; R&D Systems Inc., US).

Thrombospondin 1 was measured by (1) adding the specimen to a microplate having an anti-thrombospondin 1 monoclonal antibody immobilized thereto and allowing the reaction to proceed, and then, (2) adding labeled anti-thrombospondin 1 polyclonal antibody for the reaction to proceed. Similarly, complement factor D was measured by using an anti-complement factor D monoclonal antibody in (1), and labeled anti-complement factor D polyclonal antibody in (2).

The results of the measurement are shown in Table 4. The measurements are shown as average (mean)±standard deviation (SD). Significant difference was tested by Wilcoxon test, and the results of the Wilcoxon test (healthy subjects vs NAFLD patients) are shown according to the criteria: $+(p<0.05)$ and $++(p<0.01)$.

TABLE 4

| Factor | Healthy subject (Mean ± SD) | NAFLD (Mean ± SD) | Wilcoxon test |
|---|---|---|---|
| Thrombospondin 1 (ng/mL) | 609 ± 508 | 4733 ± 2724 | ++ |
| Complement factor D (ng/mL) | 3143 ± 516 | 4721 ± 1400 | + |

The concentration of the thrombospondin 1 and the concentration of the complement factor D in the plasma from NAFLD patients were significantly higher than the healthy subjects.

Factors in Table 2 are factors which exhibit increase of gene expression in the liver of mice exhibiting fatty liver, and protein concentrations corresponding to these factors are highly likely to increase in the plasma of human NAFLD patients compared to healthy subjects. Therefore, these factors were indicated to be candidates for the NAFLD marker measurable in blood.

Test Example 1

Method for Detecting NASH, and Method for Evaluating Therapeutic Effects on NASH, and Therapeutic Method of NASH 30 plasma specimens are collected from subjects who may be suffering from NASH, and IL-1ra, sCD40, and HMGB1 are measured and the measurements are compared with the preliminarily determined cut off value of each factor. The cut off value can be adequately determined by a medical professional before conducting the test. In this test, the cut off value is 652 (pg/mL) for IL-1ra, 17.2 (pg/mL) for sCD40, and 3.4 (ng/mL) for HMGB1.

Liver biopsy of the subjects is conducted, and NAS score (NAFLD activity score) is determined based on the seriousness of the histological findings. More specifically, the NAS score in the range of 0 to 8 is determined by evaluating steatosis (0-3), lobular inflammation (0-3), and balooning (0-2). The NAS score of 5 or higher indicates high probability of the NASH (Kleiner et al., Hepatology 2005; 41: 1313-1321).

Seriousness of the fibrosis is also scored, and NASH is diagnosed from these histological findings.

The subjects who were diagnosed as having NASH based on the histological findings exhibit value of the IL-1ra, sCD40, and HMGB1 beyond the corresponding cut off value, and therefore, NASH can be conveniently detected by measuring the IL-1ra, sCD40, and HMGB1.

Precision of the use of IL-1ra, sCD40, and HMGB1 can be improved by its combination with some of additional test indexes such as abdominal ultrasound, CT, serum lipid data (TG, HDL, LDL, TC, VLDL, etc), free fatty acid, serum 24 fractionation, blood fatty acid ratio (OA/SA ratio, EPA/AA ratio, etc.), fasting glucose, glucose after meal, HbA1c, AST, ALT, ALP, GGT, bilirubin, albumin, ferritin, thioredoxin, HOMA-IR, platelet count, TNFα, sTNF-R1, sTNF-R2, CTGF, adiponectin, leptin, high sensitivity CRP, hyaluronic acid, type IV collagen 7S, procollagen III polypeptide, CK18 fragment, and Fas.

The subject who has undergone the measurement of the marker of the present invention for NASH detection is administered for 12 months with 2700 mg/day of a preparation containing high purity EPA-E (Epadel S manufactured by Mochida Pharmaceutical Co., Ltd.) as a pharmaceutical composition containing EPAs as its effective component.

In combination with such agent, the subject with diabetes is also administered with an antidiabetic agent (thiazolidine derivative, biguanide, a glucosidase inhibitor, sulfonyl urea preparation, nateglinide, DPP-4 inhibitor, GLP-1 analog, etc.).

Before starting the administration and 1 month, 3 months, 6 months, and 12 months after the administration, the markers of the present invention, namely, IL-1ra, sCD40, HMGB1, thrombospondin 1, TIMP1, MMP12 and 13, and complement factor D are measured together with additional test indexes.

At the end of the administration, the liver biopsy of the subjects are again conducted to determine the NAS score and fibrosis level.

Before the start of the administration, the IL-1ra value of the subject is higher than the cut off value. However, the IL-1ra value is gradually reduced 1 month, 3 months, and 6 months after the administration of the EPA-E preparation with the decrease in the NAS score. Similarly, sCD40, HMGB1, thrombospondin 1, TIMP1, MMP12, MMP13, and complement factor D decrease with the administration of the EPA-E preparation.

The subject whose marker value of the present invention decreased with the administration of the NASH therapeutic agent (and/or whose marker value of the present invention approached the value of the healthy subjects) can be evaluated that NASH therapeutic effects are achieved in the subject. The change of the thrombospondin 1, TIMP1, MMP12, MMP13, and complement factor D has particularly high correlation with the therapeutic effects of the EPA-E preparation.

The additional test indexes may also be measured before the start of the administration and in the time course after the administration for use in the evaluation of the therapeutic effects.

The subjects whose NAS score is 6 or more before the start of the administration tend to show larger decrease of the NAS score (for example, decrease of 3) by the administration of the EPA-E preparation, and hence, higher therapeutic effects of the EPA-E preparation, compared to the subjects whose NAS score is 4 or less before the start of the administration.

This tendency is similar in the case of markers such as IL-1ra, sCD40, HMGB1, thrombospondin 1, TIMP1, MMP 12 and 13, and complement factor D, and subjects exhibiting a marker value higher than the preliminarily determined reference value (for example, average value of the NASH subjects) will exhibit larger decrease in the marker value and higher therapeutic effects of the EPA-E preparation. Thus, such markers as above allow the selection of subjects suitable for the treatment with an EPA-E preparation.

Accordingly, the EPA-E preparation is more preferable for treating NASH of the subjects with the NAS score of 6 or higher. In addition, the EPA-E preparation is more preferable for treating NASH of the subjects exhibiting greater degree of abnormality for the markers such as IL-1ra, sCD40, HMGB1, thrombospondin 1, TIMP1, MMP12, MMP13, and complement factor D.

The invention claimed is:

1. A method for detecting a non-alcoholic steatohepatitis (NASH) or evaluating seriousness thereof comprising:
   (A) measuring an amount and/or activity level of IL-1 receptor antagonist in a biological specimen from a subject as a marker by immunoassay; and
   (B) determining if said subject has NASH or evaluating seriousness thereof by comparing the measured value of step (A) with a cut off value, wherein the cut off value is the borderline between positive and negative of a disease, and the cut off value for said IL-1 receptor antagonist is 652 pg/mL.

2. A method for detecting a non-alcoholic steatohepatitis (NASH) or evaluating seriousness thereof comprising:
   (A) measuring an amount and/or activity level of sCD40 in a biological specimen from a subject as a marker by immunoassay; and
   (B) determining if said subject has NASH or evaluating seriousness thereof by comparing the measured value of step (A) with a cut off value, wherein the cut off value is the borderline between positive and negative of a disease, and the cut off value for said sCD40 is 17.2 pg/mL.

3. A method for detecting a non-alcoholic steatohepatitis (NASH) or evaluating seriousness thereof comprising:
   (A) measuring an amount and/or activity level of HMGB1 in a biological specimen from a subject as a marker by immunoassay; and
   (B) determining if said subject has NASH or evaluating seriousness thereof by comparing the measured value of step (A) with a cut off value, wherein the cut off value is the borderline between positive and negative of a disease, and the cut off value for said HMGB1 is 3.4 ng/mL.

* * * * *